(12) United States Patent
Saito

(10) Patent No.: US 10,251,617 B2
(45) Date of Patent: Apr. 9, 2019

(54) FLUOROSCOPIC IMAGING APPARATUS

(71) Applicant: Shimadzu Corporation, Kyoto (JP)

(72) Inventor: Tasuku Saito, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 205 days.

(21) Appl. No.: 15/322,213

(22) PCT Filed: Sep. 22, 2014

(86) PCT No.: PCT/JP2014/075142
§ 371 (c)(1),
(2) Date: Dec. 27, 2016

(87) PCT Pub. No.: WO2016/046895
PCT Pub. Date: Mar. 31, 2016

(65) Prior Publication Data
US 2017/0135658 A1      May 18, 2017

(51) Int. Cl.
*A61B 6/00* (2006.01)
*A61B 6/06* (2006.01)

(52) U.S. Cl.
CPC ............. *A61B 6/487* (2013.01); *A61B 6/06* (2013.01); *A61B 6/4233* (2013.01); *A61B 6/4435* (2013.01); *A61B 6/461* (2013.01); *A61B 6/5205* (2013.01); *A61B 6/5235* (2013.01); *A61B 6/5241* (2013.01)

(58) Field of Classification Search
CPC ........... A61B 6/487; A61B 6/486; A61B 6/06; A61B 6/4233; A61B 6/4435; A61B 6/461; A61B 6/5205; A61B 6/5235; A61B 6/5241

USPC .............................................. 378/44–46, 62
See application file for complete search history.

(56) References Cited

U.S. PATENT DOCUMENTS 6,895,076 B2 * 5/2005 Halsmer .................. A61B 6/00
378/62

FOREIGN PATENT DOCUMENTS

JP    2004236929 A    8/2004
JP    2009297284 A    12/2009

OTHER PUBLICATIONS

International Search Report dated Nov. 11, 2014 from corresponding International Application No. PCT/JP2014/075142; 7 pgs.

* cited by examiner

*Primary Examiner* — Courtney D Thomas
(74) *Attorney, Agent, or Firm* — Maier & Maier, PLLC

(57) ABSTRACT

An X-ray fluoroscopic imaging apparatus controls movement of shield plates so that a length of a first pre-image in an x direction is larger than a length of a strip image. A capturing position of the first pre-image is adjusted so that an upper end of the first pre-image matches an upper end of a capturing range of a long image. Thus, where a long region is set on the basis of the first pre-image at present, it is possible to check whether a desired X-ray image is included in a strip image. It is possible to correct a position of an imaging system to an appropriate position as an imaging start point by referring to an X-ray image included in the first pre-image having a large amount of information. Therefore, it is possible to acquire a long image appropriate for diagnosis through slot imaging using this apparatus.

3 Claims, 15 Drawing Sheets

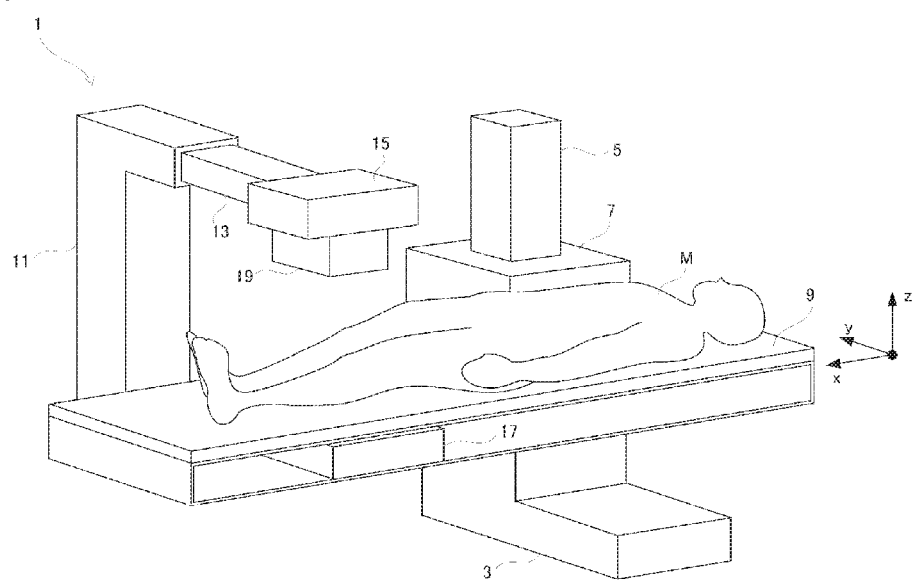
[FIG. 1]

[FIG. 2A]
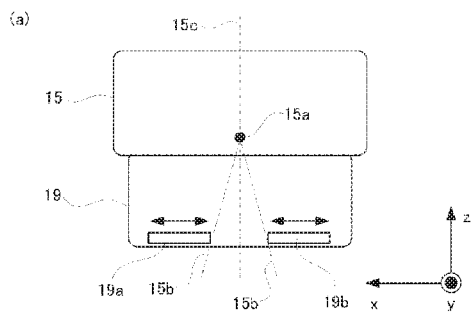
[FIG. 2B]
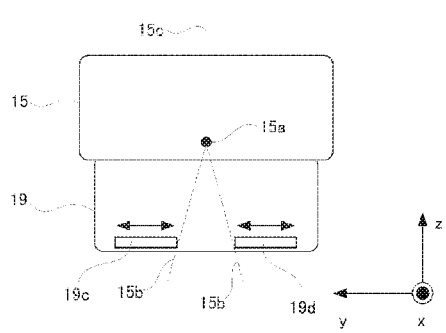
[FIG. 2C]
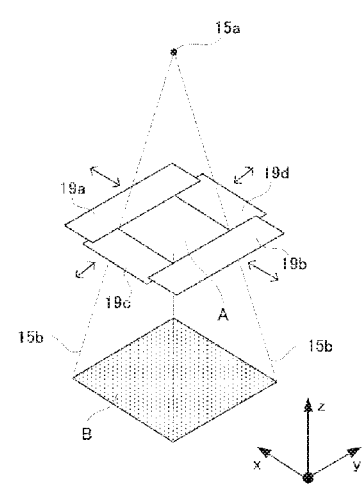

[FIG. 3]
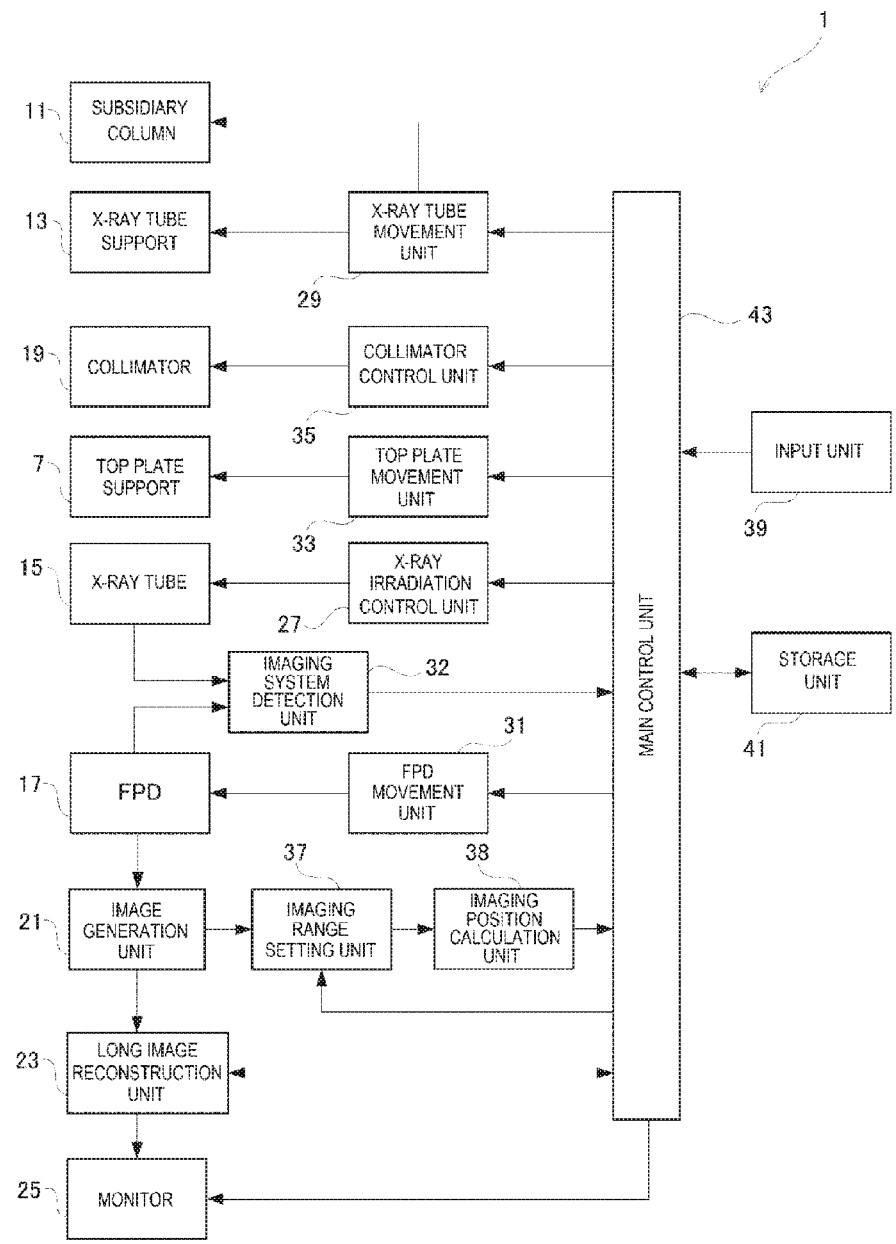

[FIG. 4A]
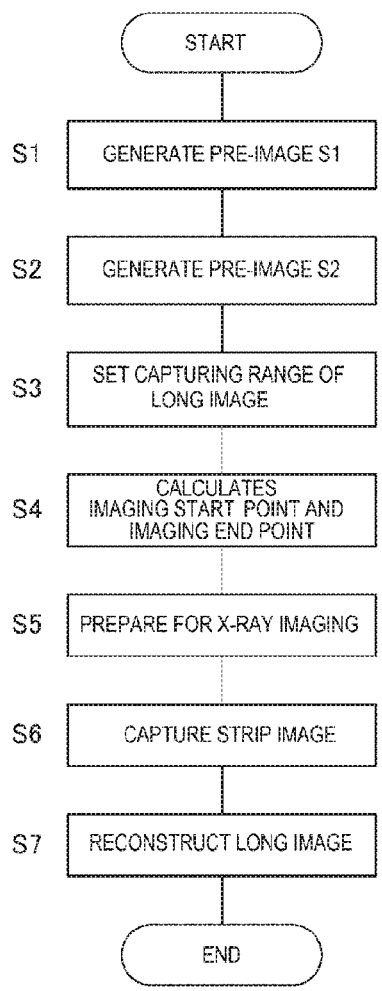
[FIG. 4B]
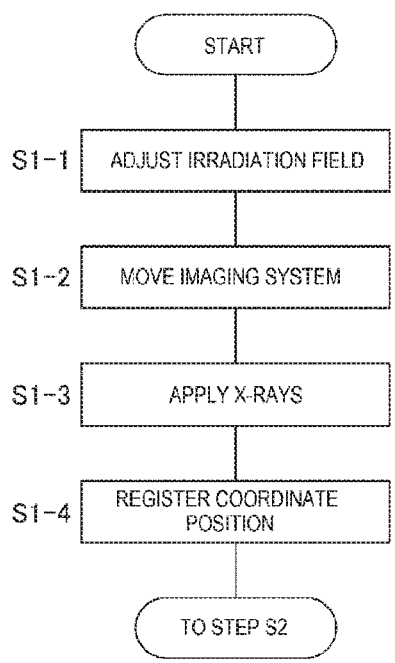

[FIG. 5A]
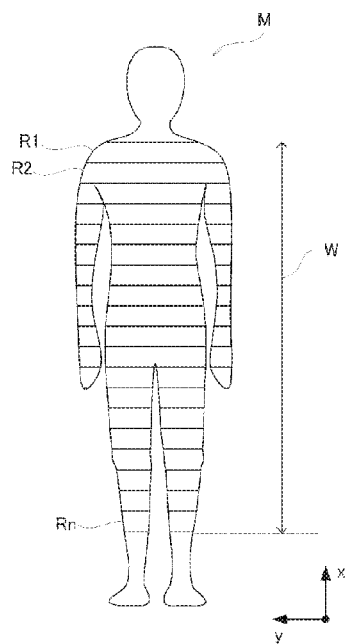
[FIG. 5B]
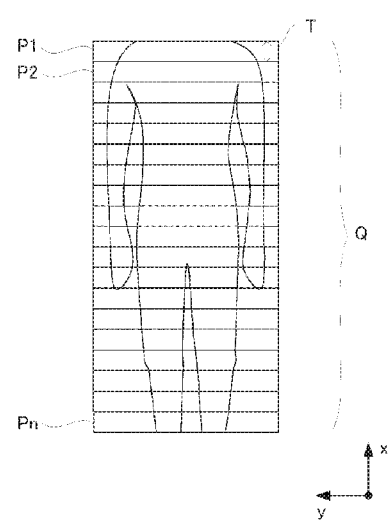

[FIG. 6A]
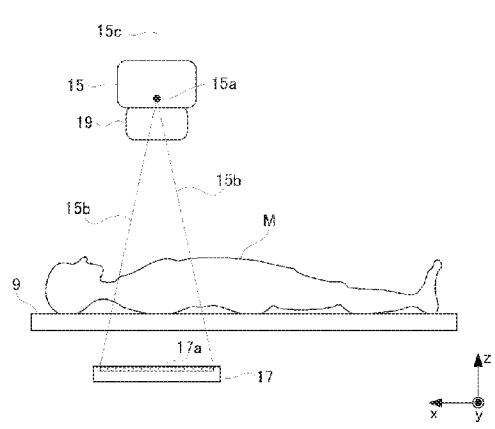
[FIG. 6B]
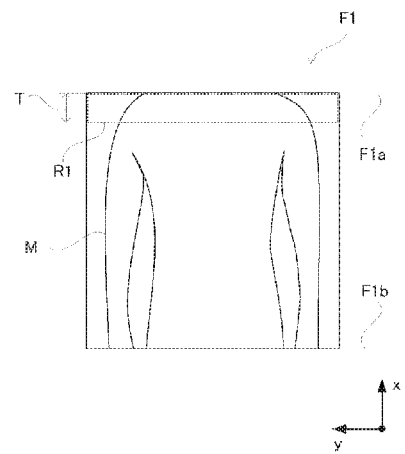

[FIG. 7A]
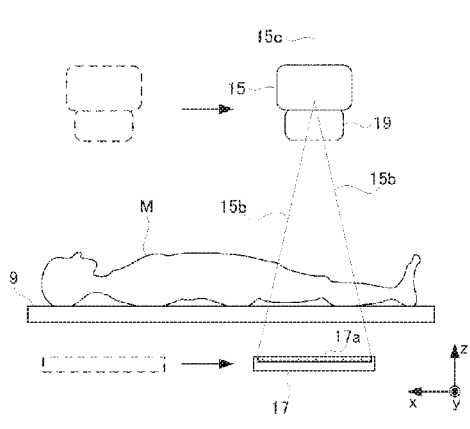
[FIG. 7B]
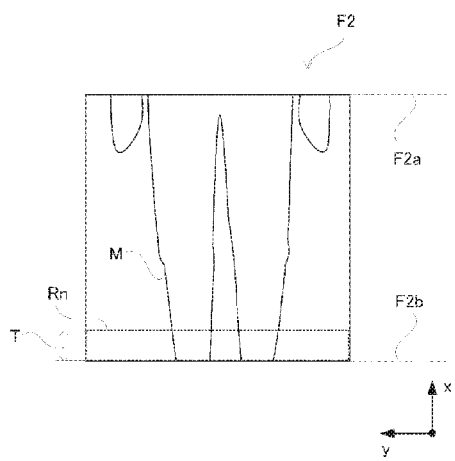

[FIG. 8A]
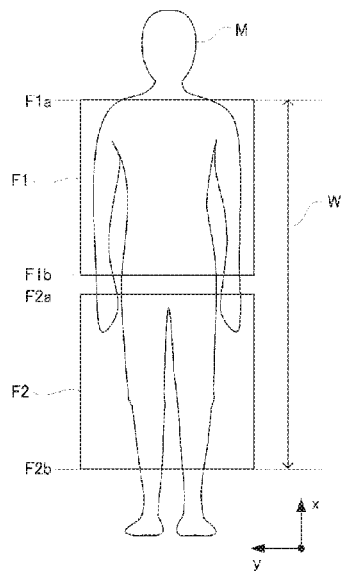
[FIG. 8B]
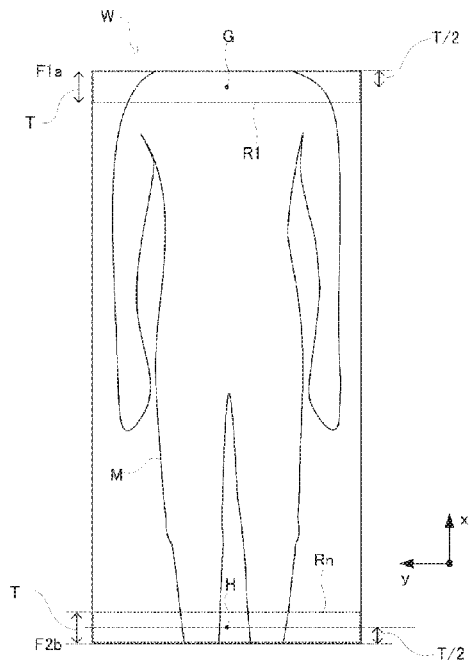

[FIG. 9A]
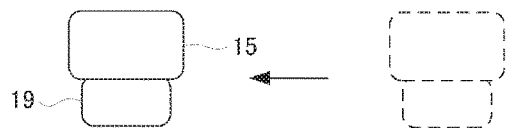
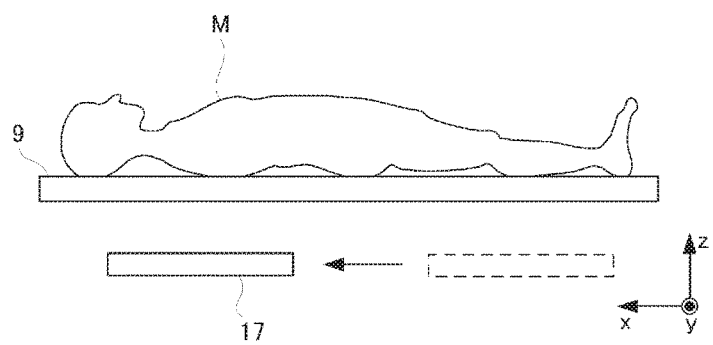
[FIG. 9B]　　　　　　　　　　　　　　[FIG. 9C]
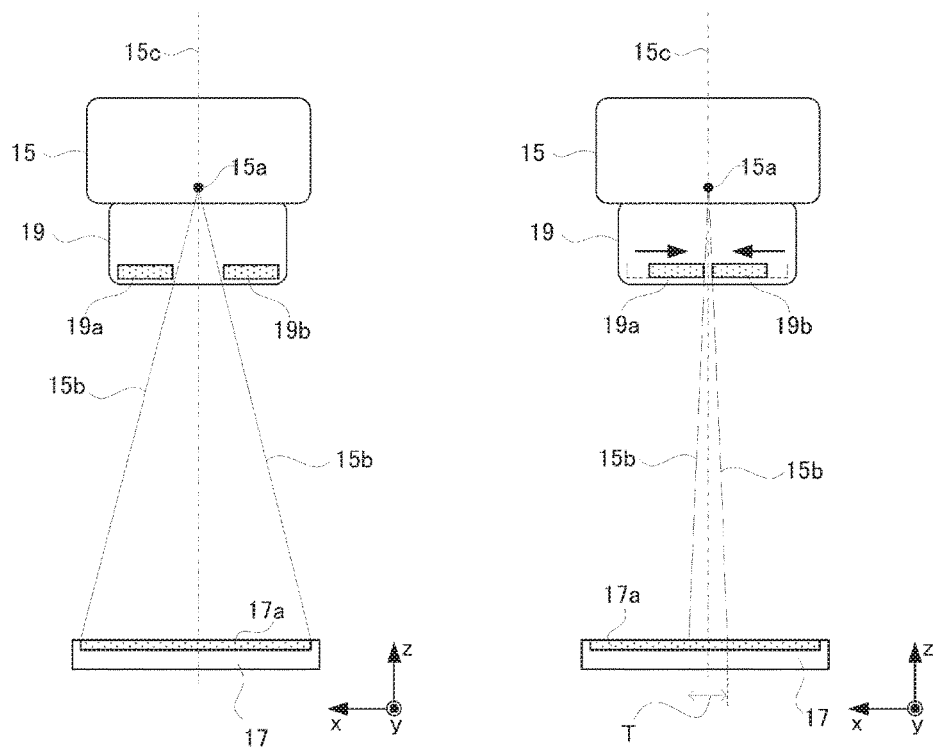

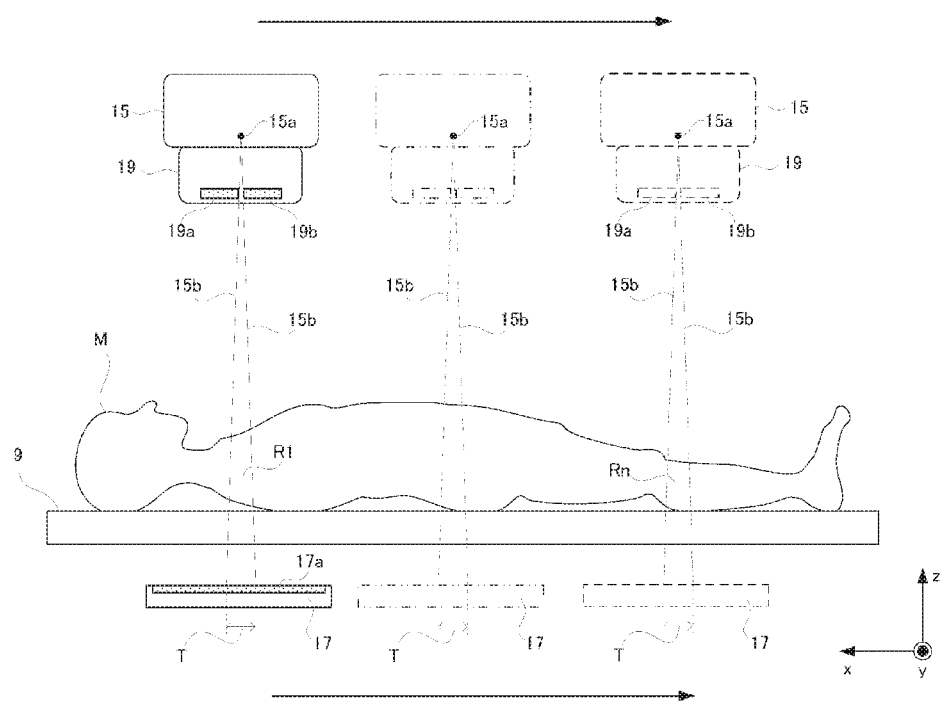
[FIG. 10]

[FIG. 11A] [FIG. 11B]
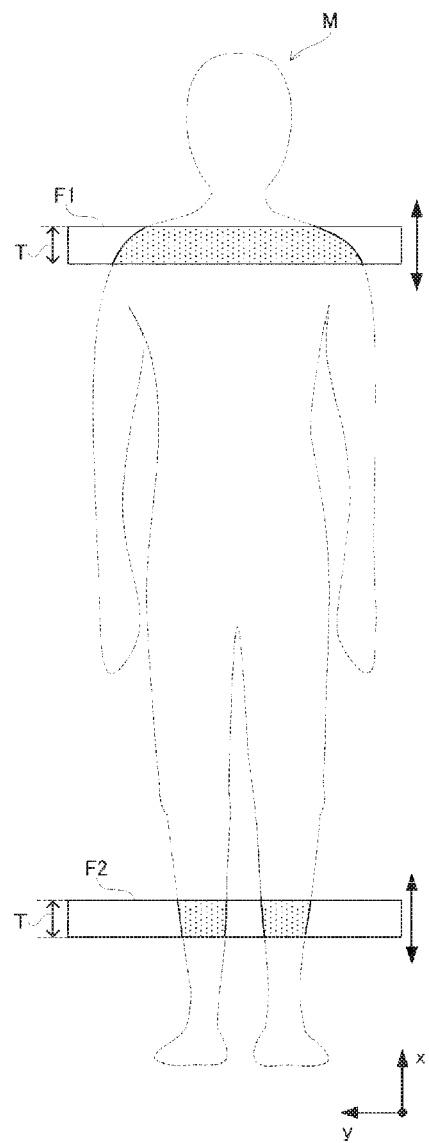
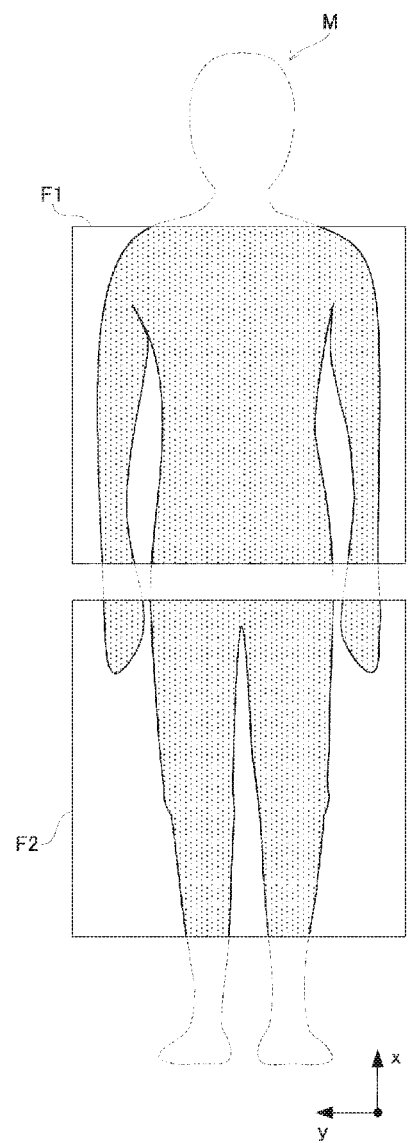

[FIG. 12A]
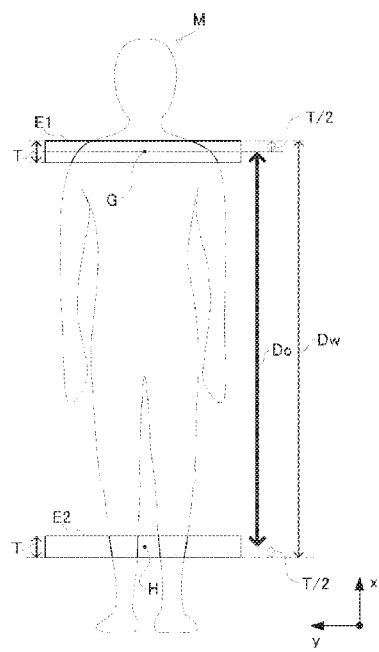
[FIG. 12B]
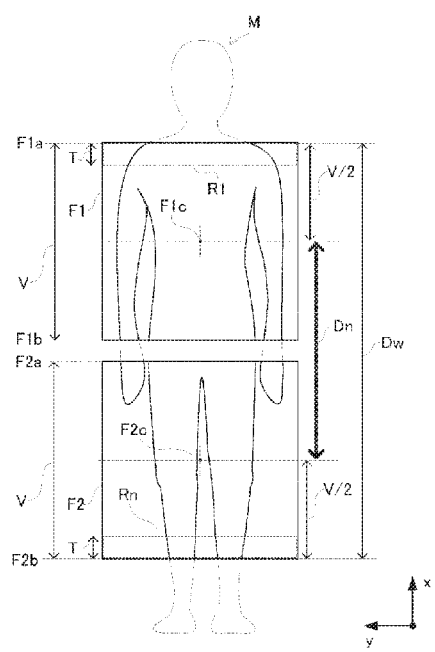

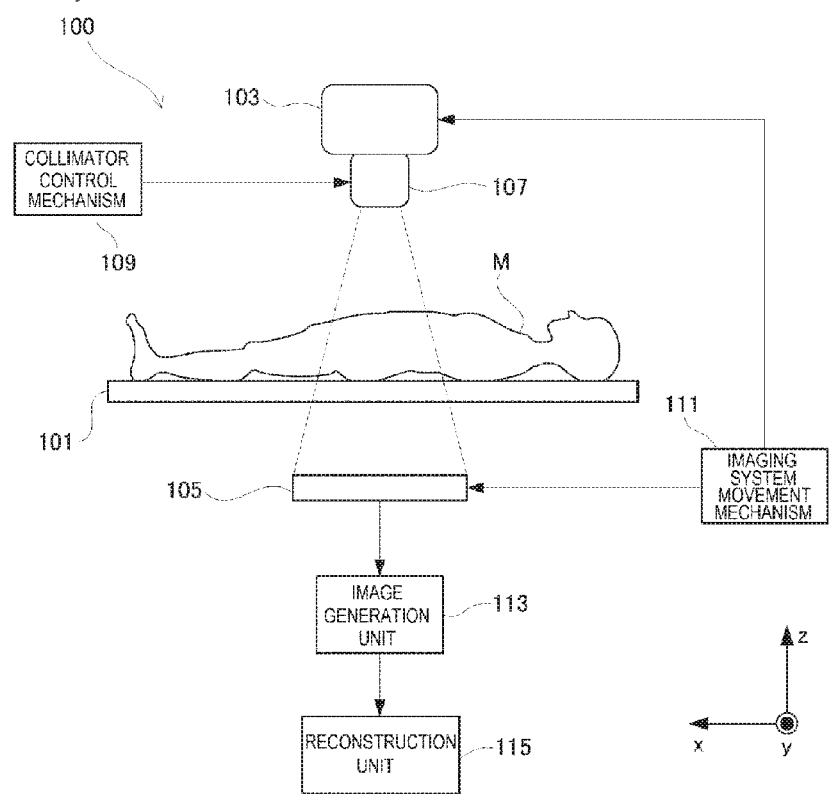
[FIG. 13]

[FIG. 14]
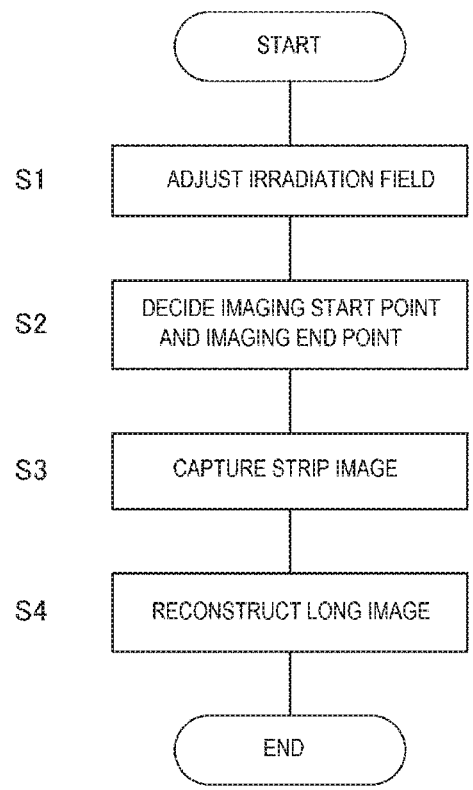

[FIG. 15A]
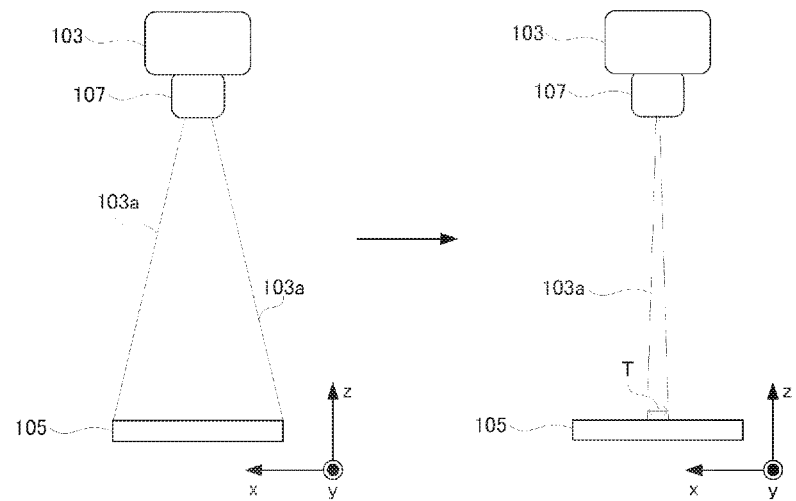
[FIG. 15B]
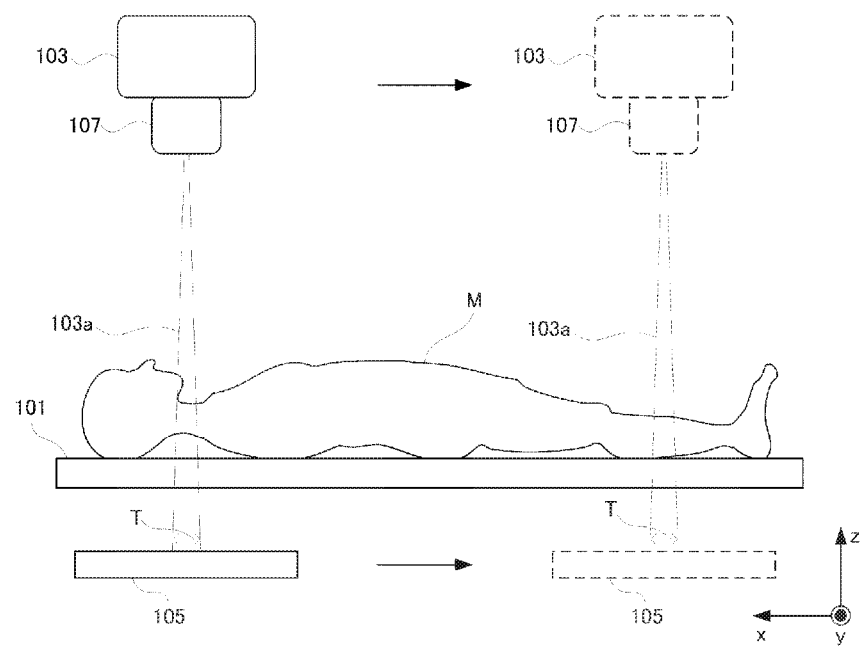

FLUOROSCOPIC IMAGING APPARATUS

TECHNICAL FIELD

The present invention relates to an X-ray fluoroscopic imaging apparatus which acquires a fluoroscopic image of a subject by using X-rays, and particularly to an X-ray fluoroscopic imaging apparatus which acquires a plurality of X-ray images and generates a single long image by joining the obtained X-ray images to each other.

BACKGROUND ART

In a medical site, long imaging may be performed in which a single X-ray image (long image) is captured by imaging a long region of a subject in a body axis direction, such as a region from the neck of the subject to the knees thereof. In this case, a length of the long region is, for example, about 100 cm, and thus it is hard to capture a long image of the long region through X-ray irradiation performed once due to the specifications of an X-ray detector. Thus, a long image is acquired according to a long imaging method in which a plurality of X-ray images are captured in the body axis direction of the subject, and the plurality of X-ray images are joined to each other in the body axis direction so as to be reconstructed. As the long imaging method, for example, slot imaging is used (for example, refer to PTLs 1 and 2).

Here, a description will be made of an X-ray fluoroscopic imaging apparatus performing slot imaging. An X-ray fluoroscopic imaging apparatus 100 of the related art performing slot imaging includes, as illustrated in FIG. 13, a top plate 101 on which a subject M is mounted, an X-ray tube 103 which irradiates the subject M with X-rays, and an X-ray detector 105 which detects X-rays. The X-ray detector 105 detects X-rays which are applied to the subject M from the X-ray tube 103 and are transmitted therethrough, and converts the X-rays into an electric signal which is then output as an X-ray detection signal.

A collimator 107 is provided under the X-ray tube 103. The collimator 107 restricts X-rays applied from the X-ray tube 103 to a pyramid shape under the control of a collimator control mechanism 109. The X-ray tube 103 and the X-ray detector 105 form an imaging system, and are disposed to oppose each other with the top plate 101 interposed therebetween. As the X-ray detector 105, for example, a flat panel detector (FPD) having a size of 17 inches square is used. Each constituent element of the imaging system is configured to be moved in an x direction, that is, a longitudinal direction of the top plate 101. Movement of each constituent element of the imaging system is controlled by an imaging system movement mechanism 111.

An image generation unit 113 is provided on the subsequent stage of the X-ray detector 105, and a reconstruction unit 115 is provided on the subsequent stage of the image generation unit 113. The image generation unit 113 generates a plurality of X-ray images on the basis of X-ray detection signals output from the X-ray detector 105. The reconstruction unit 115 joins the respective X-ray images generated by the image generation unit 113 to each other in the body axis direction of the subject M, so as to reconstruct a long image.

Next, with reference to a flowchart illustrated in FIG. 14, a description will be made of a process of performing slot imaging by using the X-ray fluoroscopic imaging apparatus 100 of the related art. The collimator 107 is driven under the control of the collimator control mechanism 109. The collimator 107 is driven, and thus an X-ray irradiation field is adjusted to be narrowed in a slit shape. If the X-ray irradiation field is adjusted, an X-ray beam 103a applied from the X-ray tube 103 is restricted as illustrated in FIG. 15(a). In other words, the X-ray beam is restricted from a pyramid shape (left part) which spreads in the x direction and the y direction (a transverse direction of the top plate 101) to a fan shape (right part) which spreads in the y direction and has a thickness T in the x direction (S1 in FIG. 14). A length of the thickness T is, for example, about 4 cm to 6 cm.

After the collimator 107 is driven, in X-ray images used to reconstruct a long image, a position (imaging start point) of the imaging system during capturing of a first X-ray image and a position (imaging end point) of the imaging system during capturing of a last X-ray image are determined (S2 in FIG. 14).

The imaging start point and the imaging end point are determined, and then an X-ray image starts to be captured. In other words, each of the X-ray tube 103 and the X-ray detector 105 is moved to the imaging start point indicated by a solid line in FIG. 15(b), and X-rays are applied from the X-ray tube 103. The X-ray detector 105 detects X-rays having been transmitted through the subject M so as to output an X-ray detection signal, and the image generation unit 113 generates an X-ray image on the basis of the X-ray detection signal. The X-ray image generated at this time is an image of a strip-shaped region having a width T corresponding to the thickness T of the X-ray beam. The strip-shaped image generated through X-ray irradiation performed once will be referred to as a "strip image".

The imaging system movement mechanism 111 moves each of the X-ray tube 103 and the X-ray detector 105 from the imaging start point to the imaging end point indicated by a dashed line in FIG. 15(b) in the x direction. The X-ray tube 103 repeatedly applies X-rays while moving a distance corresponding to the thickness T of the X-ray beam in the x direction. As mentioned above, a plurality of strip images each having the width T are generated with respect to the range from the imaging start point to the imaging end point (S3 in FIG. 14).

The reconstruction unit 115 reconstructs a single long image by joining the strip images generated by the image generation unit 113 to each other in the body axis direction (x direction) of the subject M (S4 in FIG. 14). The reconstructed long image is displayed on a monitor (not illustrated). X-rays applied when each strip image is generated spread a little in the x direction, and thus an X-ray image included in the strip image has less distortion. Therefore, it is possible to acquire a long image including an X-ray image with less distortion through slot imaging.

In a case where an imaging start point and an imaging end point of a strip image are determined, it is difficult to appropriately determine a position of the imaging start point or the like by imagining an accurate position of a structure in the body while viewing a body surface of the subject M. Therefore, in this case, in order to refer to an X-ray image scheduled to be included in a strip image, an X-ray fluoroscopic image (pre-image) of the subject M is intermittently acquired through X-ray fluoroscopy in which X-rays with a low dose are applied. An appropriate imaging start point and imaging end point are determined by referring to an X-ray image included in the acquired pre-image.

CITATION LIST

Patent Literature

[PTL 1] JP-A-2009-297284
[PTL 2] JP-A-2004-236929

SUMMARY OF INVENTION

Technical Problem

However, in a case of the example of the related art having such a configuration, there are the following problems.

That is, in a case where an imaging start point and an imaging endpoint are determined in the apparatus of the related art, in order to cause a desired X-ray image to be reliably included in a strip image, a pre-image is acquired in a state in which the collimator 107 is driven in advance and thus an X-ray beam is restricted to a capturing range of the strip image. The pre-image obtained in this case has a very small width in the body axis direction of the subject, and thus an image capturing range is narrow.

In a case where a capturing range of a pre-image is narrow, an information amount of an X-ray image obtained from the pre-image is insufficient. Thus, it is hard to predict an appropriate position of an imaging start point or an imaging end point on the basis of an X-ray image included in the pre-image. Therefore, in order to find an appropriate position of an imaging start point or an imaging end point, movement of the imaging system in the x direction and checking of a pre-image are repeatedly performed several times. As a result, the time required to decide an imaging start point and an imaging end point increases, and thus the efficiency of the long imaging is reduced. There is also concern about a problem that an amount of exposure of the subject during the long imaging increases.

In a case where an imaging start point and an imaging end point are determined in a state in which an X-ray beam is restricted to a capturing range of a strip image, each constituent element of the imaging system is required to be actually moved to the imaging start point and the imaging end point. Since the imaging start point and the imaging end point are substantially located at both ends of a capturing range of a long image, a distance which the imaging system moves is lengthened when the imaging start point and the imaging end point are decided. As a result, the time required to capture a long image increases, and thus a burden on the subject also increases.

The present invention has been made in consideration of these circumstances, and an object thereof is to provide an X-ray fluoroscopic imaging apparatus capable of performing long imaging by more accurately and rapidly determining an imaging start point and an imaging end point.

Solution to Problem

The present invention has the following configurations in order to achieve the object.

In other words, according to the present invention, there is provided an X-ray fluoroscopic imaging apparatus including an X-ray source that irradiates a subject with X-rays; X-ray detection means for detecting the X-rays having been transmitted through the subject on a detection surface thereof; a collimator that includes a shield portion blocking X-rays, and controls an irradiation field of X-rays applied from the X-ray source; collimator control means for controlling opening and closing movement of the shield portion; strip image generation means for generating a plurality of strip images each of which is a strip-shaped X-ray image having a body axis direction of the subject as a transverse direction, by using a detection signal output from the X-ray detection means; long image reconstruction means for reconstructing a single long image by joining the plurality of strip images generated by the strip image generation means to each other in the body axis direction of the subject; pre-image generation means for generating, as a pre-image, an X-ray fluoroscopic image used to set a capturing range of the long image; coordinate position storage means for storing coordinate positions of both ends of the pre-image in the body axis direction of the subject; imaging range setting means for setting positions of both ends of the capturing range of the long image in the body axis direction of the subject on the basis of the coordinate positions stored in the coordinate position storage means; and imaging position calculation means for calculating a position of an imaging start point which is a position of the imaging system when the first strip image is captured, and a position of an imaging end point which is a position of the imaging system when the last strip image is captured, on the basis of the positions of both ends of the capturing range of the long image set by the imaging range setting means, in which the collimator control means controls opening and closing movement of the shield portion so that an irradiation field of X-rays applied from the X-ray source in a case where the pre-image is generated has a wider range in the body axis direction of the subject than an irradiation field of X-rays applied from the X-ray source in a case where the strip images are generated.

According to the X-ray fluoroscopic imaging apparatus of the present invention, opening and closing movement of the shield portion is controlled so that an irradiation field of X-rays applied from the X-ray source in a case where the pre-image is generated has a wider range in the body axis direction of the subject than an irradiation field of X-rays applied from the X-ray source in a case where the strip images are generated. In other words, a size of the pre-image is larger than a size of the strip image, and thus an amount of information regarding an X-ray image included in the pre-image increases. Thus, it is possible to reliably and rapidly correct a capturing position of the pre-image to a position appropriate for setting of a capturing position of a long image by referring to the pre-image.

The coordinate position storage means stores coordinate positions of both ends of the pre-image in the body axis direction of the subject. The imaging range setting means sets positions of both ends of a capturing range of a long image in the body axis direction of the subject on the basis of the coordinate positions of both ends of the pre-image. An imaging start point and an imaging end point are calculated by the imaging position calculation means on the basis of positions of both ends of the capturing range of the long image. Therefore, it is possible to appropriately and rapidly set an imaging start point and an imaging end point in slot imaging using the X-ray fluoroscopic imaging apparatus according to the present invention.

The long image acquired through the slot imaging is an X-ray image which accurately reflects a long region as a part of interest of the subject, and thus it is possible to perform appropriate diagnosis on the long region by using the long image. It is possible to reduce the time required to acquire the long image through the slot imaging, and thus to more efficiently perform the slot imaging. It is also possible to reduce an amount of exposure of the subject M when an imaging start point and an imaging end point are set.

In the X-ray fluoroscopic imaging apparatus according to the present invention, preferably, the pre-image generation means generates a first pre-image used to set the imaging start point, and a second pre-image used to set the imaging end point; the coordinate position storage means stores a coordinate position of an end of the first pre-image on a head side of the subject, and a coordinate position of an end of the second pre-image on a foot side of the subject; and the imaging position calculation means calculates a position of the imaging start point on the basis of the coordinate position of the end of the first pre-image on the head side of the subject, and calculates a position of the imaging end point on the basis of the coordinate position of the end of the second pre-image on the foot side of the subject.

According to the X-ray fluoroscopic imaging apparatus of the present invention, the pre-image generation means generates the first pre-image used to set the imaging start point, and the second pre-image used to set the imaging end point. The coordinate position storage means stores a coordinate position of an end of the first pre-image on a head side of the subject, and a coordinate position of an end of the second pre-image on a foot side of the subject. The imaging start point is calculated on the basis of the coordinate position of the end of the first pre-image on the head side of the subject, and the imaging endpoint is calculated on the basis of the coordinate position of the end of the second pre-image on the foot side of the subject.

In this case, the number of coordinate positions used to calculate an imaging start point and an imaging end point is reduced, and thus it is possible to more simplify an operation of the coordinate position storage means or the imaging position calculation means. As a result, it is possible to more easily and rapidly calculate an imaging start point and an imaging end point.

In the X-ray fluoroscopic imaging apparatus according to the present invention, preferably, in a case where the pre-image is generated, the collimator control means controls opening and closing movement of the shield portion so that X-rays applied from the X-ray source are incident to the entire detection surface of the X-ray detection means.

According to the X-ray fluoroscopic imaging apparatus of the present invention, in a case where the pre-image is generated, the collimator control means controls opening and closing movement of the shield portion so that X-rays applied from the X-ray source are incident to the entire surface of the X-ray detection means. In this case, a size of the pre-image is large, and thus an amount of information regarding an X-ray image included in the pre-image more increases. Thus, it is possible to reliably and rapidly correct a capturing position of the pre-image to a position appropriate for setting of a capturing range of a long image by referring to the pre-image.

Advantageous Effects of Invention

According to the X-ray fluoroscopic imaging apparatus of the present invention, opening and closing movement of the shield portion is controlled so that an irradiation field of X-rays applied from the X-ray source in a case where the pre-image is generated has a wider range in the body axis direction of the subject than an irradiation field of X-rays applied from the X-ray source in a case where the strip images are generated. In other words, a size of the pre-image is larger than a size of the strip image, and thus an amount of information regarding an X-ray image included in the pre-image increases. Thus, it is possible to reliably and rapidly correct a capturing position of the pre-image to a position appropriate for setting of a capturing range of a long image by referring to the pre-image.

The coordinate position storage means stores coordinate positions of both ends of the pre-image in the body axis direction of the subject. The imaging range setting means sets positions of both ends of a capturing range of a long image in the body axis direction of the subject on the basis of the coordinate positions of both ends of the pre-image. An imaging start point and an imaging end point are calculated by the imaging position calculation means on the basis of positions of both ends of the capturing range of the long image. Therefore, it is possible to appropriately and rapidly set an imaging start point and an imaging end point in slot imaging using the X-ray fluoroscopic imaging apparatus according to the present invention.

The long image acquired through the slot imaging is an X-ray image which accurately reflects a long region as a part of interest of the subject, and thus it is possible to perform appropriate diagnosis on the long region by using the long image. It is possible to reduce the time required to acquire the long image through the slot imaging, and thus to more efficiently perform the slot imaging. It is also possible to reduce an amount of exposure of the subject M when an imaging start point and an imaging end point are set.

BRIEF DESCRIPTION OF DRAWINGS

FIG. 1 is a schematic diagram illustrating a configuration of an X-ray fluoroscopic imaging apparatus according to an embodiment.

FIG. 2A is a longitudinal sectional view illustrating a configuration when the collimator according to the embodiment is viewed in a y direction.

FIG. 2B is a longitudinal sectional view illustrating a configuration when the collimator according to the embodiment is viewed in an x direction.

FIG. 2C is a schematic diagram illustrating a configuration in which shield plates adjusts an X-ray irradiation range.

FIG. 3 is a functional block diagram illustrating a configuration of the X-ray fluoroscopic imaging apparatus according to the embodiment.

FIG. 4A is a flowchart illustrating operation processes in the X-ray fluoroscopic imaging apparatus according to the embodiment.

FIG. 4B is a flowchart specifically illustrating a process in step S1 according to the embodiment.

FIG. 5A is a diagram illustrating a region of a subject reflected in a strip image.

FIG. 5B is a diagram illustrating a long image which is reconstructed by joining strip images to each other.

FIG. 6A is a diagram illustrating a configuration of the X-ray fluoroscopic imaging apparatus in step S1.

FIG. 6B is a diagram illustrating a first pre-image acquired in step S1.

FIG. 7A is a diagram illustrating a configuration of the X-ray fluoroscopic imaging apparatus in step S2.

FIG. 7B is a diagram illustrating a second pre-image acquired in step S2.

FIG. 8A is a diagram illustrating a positional relationship between both ends of pre-images and a long region in step S3 and step S4.

FIG. 8B is a longitudinal sectional view illustrating positions of an imaging start point and an imaging end point in the long region.

FIG. 9A is a diagram illustrating an operation of an imaging system in step S5.

FIG. 9B is a longitudinal sectional view illustrating the collimator before the shield plates are moved in step S5.

FIG. 9C is a longitudinal sectional view illustrating the collimator after the shield plates are moved in step S5.

FIG. 10 is a diagram illustrating an operation of the imaging system in a process in step S6 according to the embodiment.

FIG. 11A is a diagram illustrating a capturing range of a pre-linage in the related art.

FIG. 11B is a diagram illustrating a capturing range of a pre-image according to the embodiment.

FIG. 12A is a diagram illustrating an example of the related art illustrating a distance which the imaging system moves when an imaging start point and an imaging end point are set.

FIG. 12B is a diagram illustrating a movement distance of the imaging system in the embodiment.

FIG. 13 is a schematic diagram illustrating a configuration of an X-ray fluoroscopic imaging apparatus in an example of the related art.

FIG. 14 is a flowchart illustrating processes of an operation in the X-ray fluoroscopic imaging apparatus in the example of the related art.

FIG. 15A is a diagram illustrating a shape change of an X-ray beam due to adjustment of an irradiation field.

FIG. 15B is a diagram illustrating movement of an imaging system in slot imaging in the example of the related art.

DESCRIPTION OF EMBODIMENTS

Hereinafter, an embodiment of the present invention will be described with reference to the drawings. FIG. 1 is a schematic diagram illustrating a configuration of an X-ray fluoroscopic imaging apparatus according to the embodiment.

<Description of Entire Configuration>

As illustrated in FIG. 1, an X-ray fluoroscopic imaging apparatus 1 according to the embodiment includes a base 3, a main column 5, a top plate support 7, a top plate 9, a subsidiary column 11, an X-ray tube support 13, an X-ray tube 15, an FPD 17, and a collimator 19. The main column 5 is supported at the base 3 which has a basal portion on a bottom surface, and the top plate support 7 is provided at the main column 5. The top plate 9 is supported by the top plate support 7, and allows a subject M taking a lying attitude to be mounted thereon.

The subsidiary column 11 has a basal portion at the top plate 9, and is connected to one end of the X-ray tube support 13. The X-ray tube 15 which applies X-rays is provided at the other end of the X-ray tube support 13. The FPD 17, provided under the top plate 9, detects X-rays which are applied to the subject M from the X-ray tube 15 and are transmitted therethrough, and converts the X-rays into an electric signal which is then output as an X-ray detection signal. The X-ray tube 15 and the FPD 17 form an imaging system which captures an X-ray image. The X-ray tube 15 corresponds to an X-ray source in the present invention, and the FPD 17 corresponds to X-ray detection means in the present invention.

The collimator 19 is provided under the X-ray tube 15, and includes four plate-shaped shield plates 19a to 19d. As illustrated in FIG. 2(a), the shield plate 19a and the shield plate 19b are configured to be moved in the mirror-image symmetry in an x direction (a longitudinal direction of the top plate 9) with respect to a central axis 15c of X-rays 15b which are applied from a focal point 15a of the X-ray tube 15. As illustrated in FIG. 2(b), the shield plate 19c and the shield plate 19d are configured to be moved in the mirror-image symmetry in a y direction (a transverse direction of the top plate 9) with respect to the central axis 15c of the X-rays. The respective shield plates 19a to 19d are not limited to the configuration of being moved in the mirror-image symmetry, and may have a configuration of being moved separately.

Each of the shield plates 19a to 19d is made of a material blocking X-rays, and lead may be an example of the material. As illustrated in FIG. 2(c), spread of the X-rays 15b applied from the focal point 15a of the X-ray tube 15 is restricted to a pyramid shape by each of the shield plates 19a to 19d. The X-rays 15b passing through an opening A formed by the respective shield plates 19a to 19d are applied to the subject M.

In other words, the shield plates 19a to 19d are subjected to opening and closing movement so that the opening A is adjusted, and thus a position and a range of an irradiation region B of the X-rays 15b are adjusted. The collimator 19 is provided with a visible light lamp (not illustrated), and an irradiation field of visible light applied from the visible light lamp is adjusted to match an irradiation field of the X-rays 15b applied from the X-ray focal point 15a.

As illustrated in FIG. 3, the X-ray fluoroscopic imaging apparatus 1 includes an image generation unit 21, a long image reconstruction unit 23, and a monitor 25. The image generation unit 21 is provided on the subsequent stage of the FPD 17. The image generation unit 21 forms an X-ray image of the subject M on the basis of an X-ray detection signal output from the FPD 17. An X-ray image generated by the image generation unit 21 in slot imaging includes a strip-shaped X-ray image (strip image) used to reconstruct a long image, and an X-ray fluoroscopic image (pre-image) used to set an imaging start point and an imaging end point which will be described later.

The long image reconstruction unit 23 is provided on the subsequent stage of the image generation unit 21, and reconstructs a long image by joining a series of generated strip images to each other in a body axis direction (x direction) of the subject M. The monitor 25 is provided on the subsequent stage of the long image reconstruction unit 23, and displays the reconstructed long image. The image generation unit 21 corresponds to strip image generation means and pre-image generation means in the present invention. The long image reconstruction unit 23 corresponds to long image reconstruction means in the present invention.

The X-ray fluoroscopic imaging apparatus 1 further includes an X-ray irradiation control unit 27, an X-ray tube movement unit 29, an FPD movement unit 31, an imaging system detection unit 32, a top plate movement unit 33, a collimator control unit 35, an imaging range setting unit 37, an input unit 39, a storage unit 41, and a main control unit 43. The X-ray irradiation control unit 27 is connected to the X-ray tube 15, and controls a tube voltage, a tube current, or the like of the X-ray tube 15 so as to control a dose of X-rays applied from the X-ray tube 15, a timing at which X-rays are applied, and the like.

The X-ray tube movement unit 29 is connected to the subsidiary column 11, and moves the subsidiary column 11 in the x direction (the longitudinal direction of the top plate 9, and the body axis direction of the subject M). The X-ray tube support 13 supporting the X-ray tube 15 is provided at the subsidiary column 11, and the X-ray tube 15 is thus moved in the x direction in conjunction with movement of the subsidiary column 11.

The FPD movement unit 31 moves the FPD 17 in the x direction. In other words, the imaging system formed of the X-ray tube 15 and the FPD 17 is moved in the x direction by the X-ray tube movement unit 29 and the FPD movement unit 31. The respective constituent elements of the imaging system are moved in a synchronization manner, and can be moved to a plurality of imaging positions (positions of the imaging system when capturing X-ray images) as will be described later. For example, servo motors may be used as configurations of the X-ray tube movement unit 29 and the FPD movement unit 31. The X-ray tube movement unit 29 and the FPD movement unit 31 correspond to imaging system movement means in the present invention.

A movement amount of each of the X-ray tube 15 and the FPD 17 is sequentially detected by a plurality of sensors (not illustrated) provided in each of the X-ray tube 15 and the FPD 17. A signal detected by each sensor is transmitted to the imaging system detection unit 32. An example of the sensor detecting a movement amount may include the servomotor forming each of the X-ray tube movement unit 29 and the FPD movement unit 31. The imaging system detection unit 32 sequentially detects position information of the imaging system formed of the X-ray tube 15 and the FPD 17 on the basis of a detection signal.

The top plate movement unit 33 moves the top plate support 7 in a z direction, that is, a vertical direction. The top plate 9 is supported by the top plate support 7, and is thus moved in the z direction in conjunction with movement of the top plate support 7. As an example, in a case where the subject M is moved up and down on the top plate 9, an operator moves the top plate 9 in the z direction. The collimator control unit 35 controls opening and closing movement of each of the shield plates 19a to 19d provided in the collimator 19. The imaging range setting unit 37 sets a capturing range of a long image on the basis of a pre-image generated by the image generation unit 21.

An imaging position calculation unit 38 calculates imaging positions as an imaging start point and an imaging end point of the imaging system on the basis of the capturing range of a long image set by the imaging range setting unit 37. The collimator control unit 35 corresponds to collimator control means in the present invention, and the imaging range setting unit 37 corresponds to imaging range setting means in the present invention. The imaging position calculation unit 38 corresponds to imaging position calculation means in the present invention.

The input unit 39 is used to input an instruction from the operator, and may be, for example, a keyboard input type panel or a touch input type panel. The storage unit 41 stores various parameters which are referred to for control of the X-ray fluoroscopic imaging apparatus 1, X-ray images generated by the image generation unit 21, coordinate positions of both ends of a pre-image in the x direction, which will be described later, and the like. The parameters referred to for control of the X-ray fluoroscopic imaging apparatus 1 may be, for example, parameters of a tube voltage and a tube current of the X-ray tube 15. The main control unit 43 generally controls each of the image generation unit 21, the long image reconstruction unit 23, the monitor 25, the X-ray irradiation control unit 27, the X-ray tube movement unit 29, the FPD movement unit 31, the top plate movement unit 33, the collimator control unit 35, and the imaging range setting unit 37. The storage unit 41 corresponds to coordinate position storage means in the present invention.

<Description of Operation>

Next, a description will be made of an operation in slot imaging performed by using the X-ray fluoroscopic imaging apparatus 1 according to the embodiment. FIG. 4(*a*) is a flowchart illustrating processes of an operation in slot imaging performed by using the X-ray fluoroscopic imaging apparatus 1 according to the embodiment. FIG. 4(*b*) is a flowchart specifically illustrating a process in step S1 according to the embodiment.

In this operation description, a method is described in which a plurality of elongated rectangular X-ray images each of which has the body axis direction of the subject M as a transverse direction, that is, a plurality of strip images, and a single long image is reconstructed by joining the strip images to each other in the body axis direction of the subject M. In other words, as illustrated in FIG. 5(*a*), each of regions R1 to Rn of the subject M is imaged through the imaging operation of the X-ray fluoroscopic imaging apparatus 1. As a result of X-ray imaging performed for a total of n times, as illustrated in FIG. 5(*b*), a total of n strip images P1 to Pn are generated. The strip images P1 to Pn are joined to each other in the body axis direction of the subject M, and thus a long image Q of a long region W which is a part of interest is reconstructed. A length in the transverse direction of each of the strip images P1 to Pn is indicated by T.

In the slot imaging according to the embodiment, the X-ray fluoroscopic imaging apparatus 1 images the region R1 located on the uppermost side (head side) in the body axis direction of the subject M among the regions R1 to Rn illustrated in FIG. 5(*a*), so as to generate the strip image P1. A capturing position of the strip image is sequentially moved to the lower side, and the region Rn located on the lowermost side (foot side) is imaged last, and thus the strip image Pn is generated. As illustrated in FIG. 6(*a*), it is assumed that the subject M is mounted on the top plate 9 so that the body axis direction thereof matches the x direction.

A brief description will be made of processes of an operation in the slot imaging according to the embodiment. In other words, as illustrated in FIG. 4(*a*), first, there is the generation of a first pre-image used to set a position of an end of the long region W on the head side of the subject M (step S1). Next, there is the generation of a second pre-image to set a position of an end of the long region W on the foot side of the subject M (step S2). A capturing range of the long image Q is set on the basis of the first pre-image and the second pre-image (step S3). Orders of the process related to step S1 and the process related to step S2 may be reversed to each other.

Thereafter, an imaging start point and an imaging end point are set on the basis of the capturing range of the long image (step S4). The imaging start point is a capturing position of a strip image (in the embodiment, the strip image P1) which is initially captured, and the imaging end point is a capturing position of a strip image (in the embodiment, the strip image Pn) which is captured last. The capturing position is a position taken by each constituent element of the imaging system (the X-ray tube 15 and the FPD 17) when an X-ray image is captured.

After the imaging start point and the imaging end point are set, each constituent element of the imaging system is moved to the imaging start point so as to prepare for capturing of strip images (step S5). The imaging system starts to be moved, and the strip images P1 to Pn are captured (step S6). Finally, the long image Q is reconstructed on the basis of the strip images P1 to Pn (step S7). Hereinafter, each step will be described in detail.

Step S1 (Generation of First Pre-image)

Step S1-1 (Adjustment of Irradiation Field)

In order to generate the first pre-image, first, the operator operates the input unit 39 so as to adjust an X-ray irradiation field. Position information which is input to the input unit 39 is transmitted to the main control unit 43, and the main control unit 43 outputs a control signal to the collimator control unit 35 on the basis of the transmitted information. The collimator control unit 35 moves each of the shield plates 19a to 19d provided in the collimator 19 on the basis of the control signal. Due to the movement of the shield plates 19a to 19d, as illustrated in FIG. 2(c), a position and a range of the X-ray irradiation field B are adjusted. A position and a range of the X-ray irradiation field B may be checked by using an irradiation field of visible light applied from the collimator 19.

In order to more accurately and rapidly set a position of one end of the long region W, a capturing range of the first pre-image S1 is preferably wide. Thus, adjustment is performed so that the X-rays 15b applied from the X-ray tube 15 are incident to a detection surface 17a of the FPD 17 in a wider range. Specifically, a width for applying the X-rays 15b in the x direction is preferably wider than at least the length T of the strip image in the transverse direction. Particularly, as illustrated in FIG. 6(a), adjustment is more preferably performed so that cone beam-shaped X-rays 15b are applied to the entire detection surface 17a of the FPD 17.

Step S1-2 (Movement of Imaging System)

After the X-ray irradiation field is adjusted, the operator operates the input unit 39 so as to move the imaging system. As illustrated in FIG. 5(a), the region R1 for capturing the strip image P1 corresponds to the shoulder vicinities of the subject M. Therefore, the operator checks the body surface of the subject or an irradiation field of visible light. The operator decides a rough capturing position of the first pre-image so that ends of the first pre-image and the strip image P1 on the head side of the subject M are located at the substantially same position, and inputs position information to the input unit 39.

The position information which is input to the input unit 39 is transmitted to the main control unit 43, and the main control unit 43 outputs control signals to the X-ray tube movement unit 29 and the FPD movement unit 31 on the basis of the transmitted information. The X-ray tube movement unit 29 and the FPD movement unit 31 respectively move the X-ray tube 15 and the FPD 17 to the position illustrated in FIG. 6(a) on the basis of the control signals.

Step S1-3 (Application of X-rays)

After movement of the imaging system and adjustment of the irradiation field are completed, the operator operates the input unit 39 so as to instruct X-rays to be applied. At this time, in order to reduce an amount of exposure of the subject M, X-ray irradiation conditions such as a tube voltage are input so that X-ray fluoroscopy in which an applied X-ray dose is lower than in X-ray imaging is performed. Information regarding a tube voltage or a tube current which is input to the input unit 39 is transmitted to the main control unit 43, and the main control unit 43 outputs a control signal to the X-ray irradiation control unit 27 on the basis of the transmitted information.

The X-ray irradiation control unit 27 intermittently irradiates the subject M with the X-rays 15b from the focal point 15a of the X-ray tube 15 in response to the control signal. The X-rays 15b applied from the focal point 15a are transmitted through the subject M so as to be detected by the FPD 17. The FPD 17 outputs an X-ray detection signal on the basis of the detected X-rays. The image generation unit 21 intermittently generates a first pre-image F1 on the basis of the X-ray detection signal. The generated first pre-image F1 is displayed on the monitor 25.

Step S1-4 (Registration of Coordinate Position)

The operator checks whether or not an end on the head side of the subject M in the first pre-image F1 displayed on the monitor 25 matches an end on the head side of the subject M in the region R1 for capturing the strip image P1. In a case where the ends do not match each other, the operator operates the input unit 39 as appropriate so as to move each constituent element of the imaging system in the x direction. Since positions of the shield plates 19a to 19d are adjusted so that the X-ray irradiation field is widened in step S1-2, the first pre-image F1 includes an X-ray image in a wide range of the subject M. Thus, the operator can appropriately and quickly adjust a capturing position of the first pre-image F1 by referring to the first pre-image F1 having a large amount of information.

In a case where the ends of the first pre-image F1 and the region R1 on the head side of the subject M match each other, the operator judges that the present position of the first pre-image F1 is a desired position, and registers a coordinate position. In other words, the operator operates a registration switch (not illustrated) so as to input an instruction for registering respective coordinate positions of both ends of the first pre-image F1 in the x direction. In response to the input instruction, information regarding coordinate positions in the x direction of both of the ends of the first pre-image F1 indicated by the reference signs F1a and F1b in FIG. 6(b) is stored in the storage unit 41. The coordinate position information in the x direction for both of the ends F1a and F1b is stored, and thus the processes in step S1 are all completed.

Step S2 (Generation of Second Pre-image)

After the processes in step S1 are completed, the second pre-image is generated. Processes related to step S2 are the same as the processes related to step S1. In other words, the operator operates the input unit 39 so as to adjust an X-ray irradiation field (step S2-1). An area of an X-ray irradiation field during acquisition of the second pre-image is the same as that of the X-ray irradiation field during acquisition of the first pre-image, and thus the process related to step S2-1 may be omitted as appropriate.

After the irradiation field is adjusted, the imaging system is moved (step S2-2). As illustrated in FIG. 5(a), the region Rn for capturing the strip image Pn corresponds to the knee vicinities of the subject M. Therefore, the operator checks the body surface of the subject or an irradiation field of visible light, and decides a rough capturing position of the second pre-image so that an end of the second pre-image on the foot side of the subject M is located at the substantially same position as a position of an end of the region Rn on the foot side of the subject M. The operator operates the input unit 39 so as to move the X-ray tube 15 and the FPD 17 to the position illustrated in FIG. 7(a).

After each constituent element of the imaging system is moved, X-ray are applied in a fluoroscopy mode, and thus a second pre-image F2 is generated (step S2-3). The operator moves each constituent element of the imaging system in the x direction so that the end of the second pre-image F2 on the foot side of the subject M displayed on the monitor 25 matches the end of the region Rn on the foot side of the subject M.

After the imaging system is moved so that the second pre-image F2 is located at an appropriate position, the operator operates the registration switch so as to input an instruction for registering respective coordinate positions of both ends of the second pre-image F2 in the x direction (step S2-4). In response to the input instruction, information regarding coordinate positions in the x direction of both of the ends of the second pre-image F2 indicated by the reference signs F2a and F2b in FIG. 7(b) is stored in the storage unit 41. The coordinate position information in the x direction for both of the ends F2a and F2b is stored, and thus the processes in step S2 are all completed.

Step S3 (Setting of Capturing Range of Long Image)

The processes in step S2 are completed, and then a capturing range of a long image is set. In other words, the operator operates a long region setting switch (not illustrated) provided in the input unit 39 so as to input an instruction for setting a capturing range of a long image. The imaging range setting unit 38 detects a capturing range of a long image, that is, a range of the long region W on the basis of the coordinate positions of F1a, F1b, F2a, and F2b in response to a control signal transmitted from the main control unit 43.

The range of the long region W is set on the basis of a coordinate position closest to the end on the head side of the subject M and a coordinate position closest to the end on the foot side of the subject M among the stored coordinate positions. In a case of the embodiment, as illustrated in FIG. 8(a), among the pieces of coordinate position information stored in the storage unit 41, the coordinate position of F1a closest to the end on the head side of the subject M is selected as an upper end of the long region W. The coordinate position of F2b closest to the end on the foot side of the subject M is selected as a lower end of the long region W. The coordinate positions corresponding to the upper end and the lower end of the long region W are selected as mentioned above, and thus the capturing range of a long image is set.

Step S4 (Calculation of Imaging Start Point and Imaging End Point)

After the capturing range of a long image is set, an imaging start point and an imaging end point are calculated. In other words, the operator operates the input unit 39, so as to input information regarding a length of the width T of the strip image in the transverse direction, and to instruct an imaging start point and an imaging end point to be calculated. The information regarding a length of the width T is more preferably input in advance. The imaging position calculation unit 38 calculates respective coordinate positions of an imaging start point and an imaging end point in the x direction on the basis of the instruction which is input to the input unit 39.

A description will be made of a method of calculating the coordinate positions of an imaging start point and an imaging end point with reference to FIG. 8(b). The ends (upper ends) of the region R1 and the long region W on the head side of the subject M match each other, and thus a position of the region R1 in the long region W is as illustrated in FIG. 8(b). A coordinate position of the imaging start point is the center G of the region R1, and thus a coordinate position of the imaging start point G is set to a position which is separated from the upper end of the long region W by a distance of T/2 in the x direction.

The ends (lower ends) of the region Rn and the long region W on the foot side of the subject M match each other, and thus a coordinate position of the imaging end point H is set to a position which is separated from the lower end of the long region W by a distance of T/2 in the x direction. After the first pre-image and the second pre-image are generated in the above-described way, the long region setting switch is operated, and thus the positions of the imaging start point and the imaging end point are fixed.

Step S5 (Preparation for X-ray Imaging)

After the coordinate positions of the imaging start point G and the imaging endpoint Hare set, X-ray imaging is prepared for. In other words, the operator operates the input unit 39 so as to move each constituent element of the imaging system to the imaging start point and to adjust an X-ray irradiation field. In response to an instruction input to the input unit 39, the X-ray tube 15 and the FPD 17 are moved from a capturing position of the second pre-image F2 indicated by a dashed line in FIG. 9(a) to the imaging start point indicated by a solid line.

The shield plate 19a and the shield plate 19b are moved from positions illustrated in FIG. 9(b) to positions illustrated in FIG. 9(c) in the x direction. As a result, the X-rays 15b applied from the focal point 15a are restricted from a cone beam shape (FIG. 9(b)) which spreads in the x direction and the y direction to a fan beam shape which spreads in the y direction and has the thickness T in the x direction (FIG. 9(c)). The thickness T is, for example, about 4 cm to 6 cm. Each constituent element of the imaging system is moved to the imaging start point so that the X-ray irradiation field is adjusted, and thus preparation for X-ray imaging is completed.

Step S6 (Capturing of Strip Image)

After preparation for X-ray imaging is completed, a strip image is captured. In other words, the operator operates the input unit 39 so as to apply the X-rays 15b from the focal point 15a of the X-ray tube 15. At this time, X-ray irradiation conditions such as a tube voltage are input so that X-ray imaging in which an applied X-ray dose is higher than in X-ray fluoroscopy is performed. The FPD 17 detects the X-rays 15b transmitted through the region R1 of the subject M, and outputs an X-ray detection signal. The image generation unit 21 generates the strip image P1 on the basis of the X-ray detection signal.

The X-ray tube movement unit 29 and the FPD movement unit 31 respectively move the constituent elements of the imaging system in a synchronization manner in the x direction in response to control signals output from the main control unit 43. In other words, the X-ray tube 15 and the FPD 17 are moved from the imaging start point indicated by a solid line in FIG. 10 to the imaging end point indicated by a dashed line via a position indicated by a two-dot chain line. Whenever each constituent element of the imaging system moves a distance corresponding to the width T of the strip image in the x direction, the X-ray tube 15 repeatedly applies the X-rays 15b under the control of the X-ray irradiation control unit 27.

In other words, an X-ray image of the region R1 of the subject M is included in the strip image P1 generated through first imaging, and an X-ray image of the region R2 of the subject M is included in the strip image P2 generated through the next imaging. An X-ray image of the region Rn of the subject M is included in the strip image Pn generated through last imaging. As mentioned above, the strip images P1 to Pn each having the width T in the transverse direction are generated with respect to the regions R1 to Rn of the subject M. Each constituent element of the imaging system is moved to the imaging endpoint so that the strip image Pn is generated, and thus imaging of a strip image related to step S6 is completed.

Step S7 (Reconstruction of Long Image)

After the strip images are captured, a long image is reconstructed. In other words, the long image reconstruction unit 23 reconstructs the single long image Q by joining the strip images P1 to Pn generated by the image generation unit 21 to each other in the body axis direction of the subject M.

The reconstructed long image Q is displayed on the monitor 25 and is also stored in the storage unit 41. As mentioned above, the single long image Q including the X-ray images of the long region W is acquired. The long image Q is acquired, and thus the processes related to the slot imaging are all completed.

<Effects Achieved by Configuration of Embodiment>

The configuration according to the embodiment is provided as mentioned above, and thus it is possible to efficiently acquire a long image suitable for diagnosis through slot imaging. Here, effects achieved on the basis of the configuration according to the embodiment will be described.

In the slot imaging performed by using the X-ray fluoroscopic imaging apparatus related to the example of the related art, an X-ray irradiation field is restricted to a capturing range of a strip image, and then pre-images for setting an imaging start point and an imaging end point are acquired. Positions of an imaging start point and an imaging end point are set by referring to pre-images having a size of the capturing range of a strip image.

However, in a case of the example of the related art, there is a problem in that it is hard to match positions of an imaging start point and an imaging end point of an actually acquired long image with positions of an imaging start point and an imaging end point desired by an operator. Since the time required to set an imaging start point and an imaging end point increases, there is also concern about a problem that a long image cannot be efficiently acquired by using slot imaging.

Here, with reference to the drawings, the problems of the example of the related art will be described more in detail. In the example of the related art, an X-ray irradiation field is restricted to a range which is narrow in the x direction, and then a pre-image is acquired. Thus, as illustrated in FIG. 11(a), a pre-image E1 used to set an imaging start point is generated as a strip-shaped image having the length T in the transverse direction in the same manner as a strip image. However, the length T is, for example, about 4 cm, and thus an X-ray image of the subject M included in the pre-image E1 has a narrow range indicated by dots. Thus, an information amount of the X-ray image included in the pre-image E1 is not sufficient. Therefore, it is hard for an operator to judge whether or not a capturing position of the pre-image E1 is appropriate as an imaging start point on the basis of the X-ray image included in the pre-image F1.

In this case, in order to check whether or not a capturing position of the pre-image E1 is appropriate as an imaging start point, it is necessary to move the imaging system as appropriate in a state in which X-rays are being applied. Thus, as indicated by an arrow in the figure, an operation is repeatedly performed in which a region of the subject M included in the pre-image E1 is moved in the body axis direction, and an X-ray image included in the pre-image E1 is viewed again. As a result, a problem occurs that the time required to set an imaging start point increases, and an amount of exposure of the subject M also increases. This problem similarly occurs when a pre-image E2 is generated, and an imaging end point is set.

Therefore, in the X-ray fluoroscopic imaging apparatus according to the present invention, as illustrated in FIG. 11(b), the first pre-image F1 and the second pre-image F2 are generated in a state in which an X-ray irradiation field is adjusted to a range wider than that of a strip image. Positions of an upper end and a lower end of a long region are configured to be set on the basis of the pre-images having the wide capturing range. The operator can refer to the wide-range pre-images having a large amount of information when setting positions of the upper end and the lower end of the long region. Thus, even in a case where a capturing position of the pre-image is deviated, desired X-ray images of the upper end and the lower end of the long region can be more reliably checked, and therefore each constituent element of the imaging system can be rapidly and accurately moved to an appropriate imaging position.

In the X-ray fluoroscopic imaging apparatus according to the embodiment, when an imaging start point and an imaging endpoint are set, the imaging system is moved so that an upper end or a lower end of a pre-image having a wide capturing range becomes an upper end or a lower end of a long region, and then the pre-image is acquired. Thus, it is possible to reduce a distance which each constituent element of the imaging system moves when an imaging start point and an imaging endpoint are set.

Here, with reference to FIG. 12, movement distances of the imaging system are compared with each other in the example of the related art and the embodiment. In the X-ray fluoroscopic imaging apparatus according to the example of the related art, an X-ray irradiation field is restricted to a capturing range of a strip image, and then pre-images are acquired. Thus, as illustrated in FIG. 12(a), a capturing position of the pre-image E1 used to set an imaging start point is the center G of the region R1. A capturing position of the pre-image E2 used to set an imaging end point is the center H of the region Rn. Therefore, when an imaging start point and an imaging end point are set, each constituent element of the imaging system is required to be moved from the point G to the point H. If a distance from the point G to the point H is indicated by Do, and a length of the long region W in the x direction is indicated by Dw, the distance Do is calculated according to the following Equation (1) by using the distance Dw and the distance T.

$$Do=Dw-(T/2+T/2)=Dw-T \qquad (1)$$

On the other hand, in the embodiment, as illustrated in FIG. 12(b), a capturing position of the first pre-image F1 is the center F1c of the first pre-image F1. A capturing position of the second pre-image F2 is the center F2c of the second pre-image F2. Therefore, when an imaging start point and an imaging end point are set, each constituent element of the imaging system is moved from the point F1c to the point F2c. If a distance from the point F1c to the point F2c is indicated by Dn, and a length of each pre-image in the x direction is indicated by V, the distance Dn is calculated according to the following Equation (2) by using the distance Dw and the distance V.

$$Dn=Dw-(V/2+V/2)=Dw-V \qquad (1)$$

In the embodiment, the length V of each pre-image in the x direction is set to be larger than the length T of the strip image in the x direction. Particularly, when the pre-images are generated, the X-rays 15b are preferably incident to the entire detection surface 17a of the FPD 17. Generally, a length of the detection surface 17a in the x direction is about 40 cm, and the length T of the strip image in the x direction is about 4 cm. Therefore, as an example, in a case where the length Dw of the long image in the x direction is 100 cm, when an imaging start point and an imaging end point are set, a distance which each constituent element of the imaging system moves is 96 cm in the example of the related art, but is reduced to 60 cm in the embodiment.

As mentioned above, when an imaging start point and an imaging end point are set, in the example of the related art, in order to generate a pre-image, the imaging system is required to be actually moved to an imaging start point or an imaging end point, but, in the embodiment, the imaging system is not required to be moved to an imaging start point or an imaging end point. Therefore, in the embodiment, it is possible to reduce a distance which each constituent element of the imaging system moves when an imaging start point and an imaging end point are set. As a result, it is possible to reduce the time required to set an imaging start point and an imaging endpoint and also to reduce an amount of exposure of the subject M.

As mentioned above, in the X-ray fluoroscopic imaging apparatus according to the embodiment, it is possible to appropriately and rapidly set an imaging start point and an imaging end point in slot imaging. Thus, it is possible to improve a workflow of slot imaging, and also to reduce an amount of exposure of the subject M when an imaging start point and an imaging end point are set.

The present invention is not limited to the embodiment, and may be modified as follows.

(1) In the above-described embodiment, the number of generated pre-images is two, but the number of generated pre-images may be one, or three or more. In this case, whenever the registration switch is operated, coordinate position information for both ends of the pre-image is registered. If the long region setting switch is operated, a coordinate position closest to an end of the top plate 9 on the head side of the subject M and a coordinate position closest to an end thereof on the foot side of the subject M are selected from among the registered pieces of coordinate position information, and a region having the selected coordinate positions as both ends is set as a long region. With this configuration, it is possible to flexibly cope with a variety of situations such as a registration error of a pre-image, and thus to more appropriately set a position of a long region.

(2) In the above-described embodiment, there is a configuration in which, in step S3, the long region setting switch is operated, and thus respective positions of the upper end and the lower end of the long region W are fixed, but the configuration is only an example. In other words, there may be a configuration in which, in step S1-4, when a position of the first pre-image F1 is fixed by operating the registration switch, a coordinate position of the upper end of the first pre-image F1 is registered as a coordinate position of the upper end of the long region W.

In this case, instep S2-4, when a position of the second pre-image F2 is fixed, a coordinate position of the lower end of the second pre-image F2 is registered as a coordinate position of the lower end of the long region W. With this configuration, it is possible to fix a range of the long region W in an earlier stage. It is possible to reduce an amount of information regarding coordinate positions to be registered in the storage unit 41 when the long region W is set, and thus the imaging position calculation unit 38 can more easily calculate an imaging start point and an imaging end point.

(3) In the above-described embodiment, there is a configuration in which, when a series of strip images is generated, first, the strip image P1 is captured for the region R1, and, finally, the strip image Pn is captured for the region Rn, but orders of capturing the strip images may be reversed. In this case, the capturing position of the strip image Pn is closer to a capturing position of the second pre-image F2 than the capturing position of the strip image P1, and thus it is possible to more rapidly start to capture the strip image. Thus, it is possible to reduce the time required to capture a long image.

(4) In the above-described embodiment, there is a configuration in which the X-ray tube 15 and the FPD 17 are moved in the x direction, and thus an imaging position is moved, but there may be a configuration in which the top plate movement unit 33 moves the top plate support 7 in the x direction. In this case, the top plate 9 and the subject M are moved in the x direction in conjunction with the movement of the top plate support 7. Therefore, a position of each constituent element of the imaging system relative to the subject M is displaced in the x direction in conjunction with the movement of the top plate 9.

(5) In the above-described embodiment, X-ray image capturing is performed on the subject M taking a lying attitude, but this is only an example. In other words, the configuration of the X-ray fluoroscopic imaging apparatus according to the embodiment is also applicable to a case where X-ray imaging is performed on the subject M taking a standing attitude. In this case, the x direction, that is, the body axis direction of the subject M is parallel to the vertical direction. There maybe a configuration in which the top plate 9 can be displaced from a horizontal state to a vertical state. In this case, a state of the top plate 9 is displaced as appropriate, and thus it is possible to perform X-ray imaging in both of a lying attitude and a standing attitude.

REFERENCE SIGNS LIST

1 X-RAY FLUOROSCOPIC IMAGING APPARATUS
3 BASE
5 MAIN COLUMN
7 TOP PLATE SUPPORT
9 TOP PLATE
11 SUBSIDIARY COLUMN
13 X-RAY TUBE SUPPORT
15 X-RAY TUBE (X-RAY SOURCE)
17 FPD (X-RAY DETECTION MEANS)
19 COLLIMATOR
19a TO 19d SHIELD PLATE
21 IMAGE GENERATION UNIT (STRIP IMAGE GENERATION MEANS, PRE-IMAGE GENERATION MEANS)
23 LONG IMAGE RECONSTRUCTION UNIT (LONG IMAGE RECONSTRUCTION MEANS)
29 X-RAY TUBE MOVEMENT UNIT
31 FPD MOVEMENT UNIT
33 TOP PLATE MOVEMENT UNIT
35 COLLIMATOR CONTROL UNIT (COLLIMATOR CONTROL MEANS)
37 IMAGING RANGE SETTING UNIT (IMAGING RANGE SETTING MEANS)
38 IMAGING POSITION CALCULATION UNIT (IMAGING POSITION CALCULATION MEANS)
39 INPUT UNIT
41 STORAGE UNIT (COORDINATE POSITION STORAGE MEANS)
43 MAIN CONTROL UNIT

The invention claimed is:

1. An X-ray fluoroscopic imaging apparatus, comprising:
an X-ray source that irradiates a subject with X-rays;
X-ray detection means for detecting the X-rays having been transmitted through the subject on a detection surface thereof;
a collimator that includes a shield portion blocking X-rays, and controls an irradiation field of X-rays applied from the X-ray source;
a collimator control means for controlling opening and closing movement of the shield portion;
strip image generation means for generating a plurality of strip images each of which is a strip-shaped X-ray image having a body axis direction of the subject as a transverse direction, by using a detection signal output from the X-ray detection means;

long image reconstruction means for reconstructing a single long image by joining the plurality of strip images generated by the strip image generation means to each other in the body axis direction of the subject;

pre-image generation means for generating, as a pre-image, an X-ray fluoroscopic image used to set a capturing range of the long image;

coordinate position storage means for storing coordinate positions of both ends of the pre-image in the body axis direction of the subject;

imaging range setting means for setting positions of both ends of the capturing range of the long image in the body axis direction of the subject on the basis of the coordinate positions stored in the coordinate position storage means; and imaging position calculation means for calculating a position of an imaging start point which is a position of an imaging system when the first strip image is captured, and a position of an imaging end point which is a position of the imaging system when the last strip image is captured, on the basis of the positions of both ends of the capturing range of the long image set by the imaging range setting means, wherein the collimator control means controls opening and closing movement of the shield portion so that an irradiation field of X-rays applied from the X-ray source in a case where the pre-image is generated has a wider range in the body axis direction of the subject than an irradiation field of X-rays applied from the X-ray source in a case where the strip images are generated wherein a range of the strip images, in the body axis direction of the subject of the irradiation field of X-rays applied from the X-ray source, is set before the pre-image is generated.

2. The X-ray fluoroscopic imaging apparatus according to claim 1, wherein the pre-image generation means generates a first pre-image used to set the imaging start point, and a second pre-image used to set the imaging end point, wherein the coordinate position storage means stores a coordinate position of an end of the first pre-image on a head side of the subject, and a coordinate position of an end of the second pre-image on a foot side of the subject, and wherein the imaging position calculation means calculates a position of the imaging start point on the basis of the coordinate position of the end of the first pre-image on the head side of the subject, and calculates a position of the imaging end point on the basis of the coordinate position of the end of the second pre-image on the foot side of the subject.

3. The X-ray fluoroscopic imaging apparatus according to claim 1, wherein, in a case where the pre-image is generated, the collimator control means controls opening and closing movement of the shield portion so that X-rays applied from the X-ray source are incident to the entire detection surface of the X-ray detection means.

* * * * *